(12) United States Patent
Polzius et al.

(10) Patent No.: US 8,701,815 B2
(45) Date of Patent: Apr. 22, 2014

(54) DRUG INTERLOCK SYSTEM HAVING A SAFETY FUNCTION

(75) Inventors: Rainer Polzius, Lübeck (DE); Stefan Morley, Lübeck (DE); Michael Reinhart, Stockelsdorf (DE)

(73) Assignee: Dräger Safety AG & Co. KGAA, Lübeck (DE)

( * ) Notice: Subject to any disclaimer, the term of this patent is extended or adjusted under 35 U.S.C. 154(b) by 0 days.

(21) Appl. No.: 13/823,358

(22) PCT Filed: Sep. 29, 2011

(86) PCT No.: PCT/EP2011/004877
§ 371 (c)(1),
(2), (4) Date: Mar. 14, 2013

(87) PCT Pub. No.: WO2012/041505
PCT Pub. Date: Apr. 5, 2012

(65) Prior Publication Data
US 2013/0168175 A1    Jul. 4, 2013

(30) Foreign Application Priority Data
Sep. 30, 2010    (DE) .......................... 10 2010 047 177

(51) Int. Cl.
*B60K 28/06*    (2006.01)
(52) U.S. Cl.
USPC ......................................... 180/272; 340/576
(58) Field of Classification Search
USPC ............. 180/272, 273, 287; 340/576; 701/36, 701/45, 113
See application file for complete search history.

(56) References Cited

U.S. PATENT DOCUMENTS 5,793,292 A * 8/1998 Ivey, Jr. .......................... 340/576
5,969,615 A * 10/1999 Ivey et al. ...................... 340/576
6,022,326 A    2/2000 Tatum et al.
(Continued)

FOREIGN PATENT DOCUMENTS

DE    197 42 261 A1    4/1999
WO    2009/083964 A2    7/2009

OTHER PUBLICATIONS

Studies on Hashish. IV Colour reactions of Cannabinols, Qual. Plant. Mater. Veg. XXII: 7-13, 1972.
Analysis of Cannabinoids, Research Monographs 42, NIDA, 1982.
(Continued)

*Primary Examiner* — Paul N Dickson
*Assistant Examiner* — Laura Freedman
(74) *Attorney, Agent, or Firm* — McGlew and Tuttle, P.C.

(57) ABSTRACT

An interlock system for a vehicle includes a sampling device (4) that receives a sufficient quantity of a body fluid sample from a person to be tested; a read-out unit (11) detecting substances that are contained in the body fluid sample; and an evaluating unit (2) evaluating the substances detected by the read-out unit (11), so that respective concentrations of the detected substances can be obtained. The detection and evaluation of the substances in the body fluid is effected by chemical, immunochemical, enzymatic, electrochemical or optical analytical methods. The quantity of body fluid delivered by the person to be tested is automatically detected and monitored. A control device (1) is coupled to the evaluating unit (2) and prevents the start process of the vehicle if an insufficient quantity of body fluid is present or if at least one of the substance concentrations is above a predetermined concentration limit value.

20 Claims, 4 Drawing Sheets

(56) References Cited

U.S. PATENT DOCUMENTS

| | | | |
|---|---|---|---|
| 6,075,444 A * | 6/2000 | Sohege et al. | 340/576 |
| 6,886,653 B1 * | 5/2005 | Bellehumeur | 180/272 |
| 7,256,700 B1 | 8/2007 | Ruocco et al. | |
| 7,413,047 B2 * | 8/2008 | Brown et al. | 180/272 |
| 7,671,752 B2 * | 3/2010 | Sofer | 340/576 |
| 7,888,130 B2 * | 2/2011 | Wuske et al. | 436/169 |
| 7,909,128 B1 * | 3/2011 | Pontillo | 180/272 |
| 7,932,082 B2 * | 4/2011 | Abraham-Fuchs et al. | 435/309.1 |
| 8,240,419 B2 * | 8/2012 | Zimmermann et al. | 180/272 |
| 8,256,286 B2 * | 9/2012 | Carroll et al. | 73/335.04 |
| 8,469,135 B2 * | 6/2013 | Kaschner | 180/272 |
| 2004/0022687 A1 | 2/2004 | Wuske et al. | |
| 2004/0083031 A1 * | 4/2004 | Okezie | 701/1 |
| 2006/0033628 A1 * | 2/2006 | Duval | 340/576 |
| 2006/0173256 A1 | 8/2006 | Ridder et al. | |
| 2007/0273537 A1 | 11/2007 | Crespo et al. | |
| 2011/0050407 A1 * | 3/2011 | Schoenfeld et al. | 340/426.11 |
| 2012/0073892 A1 * | 3/2012 | Hunter | 180/273 |

OTHER PUBLICATIONS

"Determination of narcotic and psychotropic substances by using infrared spectroscopy," Middle East Technical University, Jul. 2005 (http:/etd.metu.edu.tr/upload/12606293/index.pdf).

"NHTSA Report DOT HS 811 249 2007 National Roadside Survey of Alcohol and Drug Use by Drivers: Drug Results,".

\* cited by examiner

DRUG INTERLOCK SYSTEM HAVING A SAFETY FUNCTION

CROSS REFERENCE TO RELATED APPLICATIONS

This application is a United States National Phase application of International Application PCT/EP2011/004877 and claims the benefit of priority under 35 U.S.C. §119 of German Patent Application DE 10 2010 047 177.1 filed Sep. 30, 2010, the entire contents of which are incorporated herein by reference.

FIELD OF THE INVENTION

The present invention generally pertains to a device that is designed to prevent a vehicle from being started or a machine from being operated by a driver or user, respectively, who is under the influence of drugs. Such a device will hereinafter be called "drug interlock system" and embodies, in general, the combination of a drug-measuring device as well as an immobilizer for a motor vehicle, a blocking means for a machine or correspondingly also a starting means for a machine or an actuating means for a motor vehicle, which is released only if certain permissible conditions are met.

BACKGROUND OF THE INVENTION

So-called alcohol interlock systems are known from the state of the art, which are used to prevent a driver who is under the influence of alcohol following a positive alcohol measurement from starting the engine of a motor vehicle (passenger car, truck, bus, etc.), from operating a machine or from entering a secured area in a company. Such an alcohol interlock system contains essentially an alcohol-measuring device, which is installed, as a rule, permanently in the interior of the vehicle, as well as a control device, which is coupled to the alcohol-measuring device and which is installed permanently, for example, under the instrument panel of the vehicle and is designed to release or block the power supply to the starter of the vehicle. The alcohol-measuring device is preferably a breath alcohol-measuring device, which is designed as a hand-held device and is connected to the control device via an electric connection cable.

These prior-art alcohol interlock systems are also in use in large numbers in so-called offender programs, in which persons are only permitted to drive a vehicle under the condition that they allow such a system to be installed in their vehicle. These conditions are, in general, subject to a time limitation, and the systems are removed from the vehicle after the end of that period. Alcohol interlock systems thus represent a cost-effective alternative to a possible prison sentence or (in most cases) to the revocation of the driver's license to the state and also for the driver, who is sentenced, for example, because of drunkenness. Since the drivers who have been sentenced usually have to install an alcohol interlock system for a limited time period only, such systems are usually leased to the drivers in these so-called offer programs. Consequently, only the costs for the lease payment and possibly costs for the special mouthpieces are incurred.

Methods for determining substances in body fluids are known as well. The corresponding detection methods comprise chemical, biochemical, electrochemical and optical methods. For example, the specific reaction of cannabinoids with Gibbs reagent, which can be detected either directly by color reaction or indirectly by electrochemical detection, is known (Studies on Hashish. IV Colour reactions of Cannabinols, Qual. Plant. Mater. Veg. XXII: 7-13, 1972). The direct electrochemical detection of cannabis preferably following chromatographic separation of the components of the sample has been described as well (Analysis of Cannabinoids, Research Monographs 42, NIDA, 1982). The optical properties of common drugs are described together with a review of measuring techniques, e.g., in the study of zlem Baran: "Determination of narcotic and psychotropic substances by using infrared spectroscopy," Middle East Technical University, July 2005 (http:/etd.metu.edu.tr/upload/12606293/index.pdf). Especially immunochemical methods are used for the trace analysis of medicinal drugs or illegal drugs from body fluids, for example, blood, urine, sweat or saliva.

When collecting body fluids, it is rather important to collect and make available a sufficient quantity or a sufficient volume of body fluid for the necessary analysis. For example, when drawing blood, the quantity of blood drawn can be checked easily by means of the scale of the syringe or, when urine is used, by means of the scale on the measuring vessel. In case of tests based on saliva, the filling level can be displayed, e.g., by a color change of the sampler when a desired quantity is reached. The decision on whether or not a sufficient quantity of body fluid is available is not made by the person to be tested but by the person (for example, a physician), who performs the test. For comparison, the volume measurement is performed by a gas flow sensor in the device in case of breath alcohol-measuring devices.

The above methods are used as rapid tests for the occupational medical monitoring of persons at hazardous workplaces or even for testing automobile drivers during roadside checks.

As is described in the "NHTSA Report DOT HS 811 249 2007 National Roadside Survey of Alcohol and Drug Use by Drivers: Drug Results," the consumption of drugs is also a frequently occurring offence during the operation of motor vehicles, besides the consumption of alcohol. It is therefore desirable, in principle, to test vehicle drivers not only for alcohol consumption, but also for the consumption of drugs, and to prevent a vehicle from being started in case of drug consumption.

An alcohol interlock device, which carries out an alcohol test on the basis of a saliva sample, is known from WO 2009/083964 A2. The giving of a sufficient quantity of saliva is either assumed as given by a person for a sample holder inserted into the mouth after the end of a certain time or read on the basis of the filling level of a capillary receiving the saliva. The interlock device may also be modified in order to test the saliva for drugs. This interlock device has the drawback that errors of measurement may occur when a measurement is carried out with an insufficient quantity of saliva, because this could cause a lower alcohol concentration to be measured than is actually present in the body.

There also is, in principle, a possibility of tampering with all prior-art interlock systems due, for example, to a sample requested by the system being given by a second person, who is not the person who is to be tested. In order to eliminate such a possibility of circumvention, prior-art alcohol interlock systems usually have an alcohol measurement repeat function. This means that the interlock system prompts the driver again after a randomly generated interval of time to perform an alcohol measurement. Tampering shall be made at least difficult in this manner.

DE 197 42 261 A1 describes a device for blocking the operation of a vehicle by a driver who is under the influence of alcohol. The alcohol-measuring device is designed to be attached to a body part (arm or leg) of the driver and to be able to measure the driver's alcohol level by means of an electrochemical gas sensor on the basis skin permeation. The analyzing unit proper of the device, via which the vehicle is released or blocked, is mounted permanently in the vehicle and communicates with the measuring device in a wireless manner.

U.S. Pat. No. 7,256,700 B1 pertains to an interlock system, by means of which a vehicle is prevented from being started by a driver who is under the influence of alcohol. The interlock system is coupled to a mobile telephone or a similar communications means, with which a failed alcohol measurement is communicated by a voice message being sent via the mobile telephone. Furthermore, data, which are stored in the interlock system, can also be sent over the mobile telephone.

US 2007/0273537 A1 discloses a combined testing and localization system, which contains, among other things, an interlock system. The interlock system is used in the known manner to prevent a vehicle from being started by a driver who is under the influence of alcohol. The system is equipped, furthermore, with an EMHA system (Electronic Monitoring Home Arrest), which can communicate with a remote server, for example, via a mobile telephone. However, data being stored in the interlock system can also be transmitted to the server via this mobile telephone.

US 2006/0173256 A1 pertains to an interlock system to prevent a vehicle or a machine from being operated by a person who is under the influence of alcohol. Methods and devices for the noninvasive measurement of alcohol and other substances are used for this.

Many of the events relevant for the use, for example, data, time, the giving of a sample, values measured for the sample, engine starts and stops, as well as attempts at tampering with the interlock system, can be recorded in a memory of the interlock system during the use of the vehicle. These data can be compiled into a protocol and read, for example, by means of a data cable. The reading may be carried out, for example, in an authorized workshop or on site by an authorized mechanic.

One drawback of the prior-art interlock systems is that they cannot be deactivated or reactivated from a remote center. Should, for example, the vehicle be prevented from being started because of a technical defect of the interlock system or based on a malfunction of the detection system, the driver is consequently unable to start his vehicle without the aid of another person. The defective interlock system can be released or deactivated in such a case on site only at the interlock system of the vehicle itself by an authorized mechanic entering a secret release code into the interlock system, for example, by means of a computer, which is connected to a corresponding interface of the interlock system via a data cable, as a result of which the interlock system is released or deactivated and the engine of the vehicle can again be started. As an alternative, the interlock system must be repaired and reactivated in a workshop.

SUMMARY OF THE INVENTION

An object of the present invention is to provide an advantageous interlock system, with which the concentration of drugs or other substances contained in a body fluid can be determined and which is designed to prevent, for example, a motor vehicle from being started in case of a positive detection result.

According to the invention, an interlock system is provided for a vehicle, with a sampling device, which is designed to receive a sufficient body fluid sample from a person to be tested, a read-out unit, which can be coupled to the sampling device, for detecting substances that are contained in the body fluid sample and a first analyzing unit (evaluating unit) that can be coupled to the read-out unit for analyzing the substances detected by the read-out unit to obtain respective concentrations of the detected substances. The detection and analysis of the substances in the body fluid is carried out by means of chemical, immunochemical, enzymatic, electrochemical or optical detection methods. A measuring arrangement is also provided for the automatic measurement of measured data, which are an indicator of the quantity of body fluid received by the sampling device. The measuring arrangement is designed to transmit the measured data to a second analyzing unit (evaluating unit). The second analyzing unit is designed to determine, on the basis of the measured data, whether the quantity of body fluid received by the sampling device exceeds a predetermined limit value. A control device, which can be coupled to the first analyzing unit and the second analyzing unit, is designed to prevent the vehicle start process if the quantity of body fluid received does not exceed the limit value or if at least one of the substance concentrations is above or below a predetermined concentration limit value.

It should be noted that the interlock system according to the present invention is called a "drug interlock system" in this specification. However, this interlock system may be additionally designed to also detect other illegal substances, for example, alcohol, besides drugs.

The interlock system according to the present invention for a vehicle comprises:
  a sampling device, which is designed to take a sufficient body fluid sample from a person to be tested;
  a read-out unit, which can be coupled to the sampling device, for detecting substances that are contained in the body fluid sample;
  a first analyzing unit, which can be coupled to the read-out unit, for analyzing the substances detected by the read-out unit, in order to obtain the respective concentration of the substances detected, wherein the detection and analysis of the substances in the body fluid is carried out by means of chemical, immunochemical, enzymatic, electrochemical or optical detection methods;
  a measuring arrangement for the automatic measurement of measured data, which are an indicator of the quantity of body fluid obtained by the sampling device, the measuring arrangement being designed to transmit the measured data to a second analyzing unit and the second analyzing unit being designed to determine on the basis of the measured data whether the quantity of body fluid obtained by the sampling device exceeds a predetermined limit value; and
  a control device, which can be coupled to the first analyzing unit and the second analyzing unit, and which is designed to prevent the vehicle start process if the quantity of body fluid obtained does not exceed the limit value or if at least one of the substance concentrations is above or below a predetermined concentration limit value.

The drug interlock system according to the present invention operates, in principle, as follows: After the ignition of the vehicle has been switched on, the drug interlock system prompts the driver to give a sample. The result of the determination of the quantity of the body fluid obtained and the measured drug concentration in that sample decide, independently from one another, whether the starter of the vehicle will be released and the engine can be started. The engine is prevented from being started if at least one of the following situations is present:

The quantity of body fluid obtained does not exceed the predetermined limit value, at least one of the substance concentrations is above or below a predetermined concentration limit value.

In other words, the engine can only be started if neither of the two situations is present.

Due to the automatic detection of the quantity of body fluid obtained, a person monitoring the sampling, who ensures that the quantity of liquid given is sufficient to obtain a reliable result of measurement for the concentration of the substance to be detected, is not necessary. The drug interlock system according to the present invention can therefore be operated autarchically especially in a motor vehicle.

As was explained above, the drug interlock system according to the present invention is a drug-measuring device combined with a vehicle immobilizer. The purpose of the drug interlock system according to the present invention is, in principle, to prevent a driver who is under the influence of drugs from starting the engine of the vehicle in which the interlock system is installed. As an alternative, the engine of the vehicle is only released for the start process or operation if the result of the drug test is negative, i.e., no relevant drug concentration is measured. Drug-related accidents can be prevented due to the installation of the interlock system. Furthermore, the interlock system is suitable for supporting long-term changes in the driver's behavior in regard to his contact with drugs or other substances.

The body fluid is advantageously blood, urine, saliva, tear fluid, sweat or interstitial tissue fluid.

According to one variant, the temperature of the body fluid given is measured during the giving of the sample and is compared with a range of desired values.

A body fluid given by a person to be tested directly into the sampling device has a temperature that is in a range of desired values. A body fluid had been given, for example, before drugs were taken and stored in a container for a rather long time has a temperature that is no longer in the range of desired values. This can be utilized to make an analysis of the body fluid and thus the starting of the vehicle contingent on whether or not the temperature is in the range of desired values. A range of desired values can be determined for each body fluid that can be analyzed by the interlock system, for example, on the basis of empirical data.

In one embodiment of the present invention, the measured data represent a measure of a color change of a detection zone of the sampling device, of a change in the refractive index of a detection zone of the sampling device, of electrochemical properties of the body fluid or of the conductivity of the body fluid.

A quantity of body fluid sufficient for an analysis is present if a corresponding color change takes place, there is a certain change in the refractive index, or if the electrochemical properties or the conductivity of the body fluid are in a respective preset range of parameters or are above or below a limit value.

The substances advantageously belong to a group that comprises illegal drugs, for example, amphetamines, methamphetamines, opiates, cocaine, cannabinoids, or to a group that comprises therapeutic drugs, for example, benzodiazepines, methadone, buprenorphine and tricyclic antidepressants.

In one variant, sampling is monitored by means of a camera by determining optically whether a mouthpiece of the sampling device is in the mouth of the driver during sampling.

Sampling is advantageously monitored by determining by biochemical detection reactions whether the sample is human saliva or the saliva of the individual driver.

It is advantageous to determine the times at which a measurement takes place, for example, before the driving or during driving by means of a random generator.

Fraudulent tampering with the interlock system is made difficult by each of the variants mentioned in the last three paragraphs. This means that the probability that the driver is indeed drug-free in case of a negative analytical result increases as the number of these measures taken simultaneously increases.

The sampling device is advantageously designed to be inserted into the control device or into a hand-held device connected to the control device.

Provisions are made in one variant of the present invention for the control device to have a first relay, which is coupled to the starter of the vehicle, is switched depending on the substance concentration measured and in the presence of which relay the control device has a second relay, which is connected in parallel to the first relay and can be switched in response to data received in a wireless manner.

Deactivation (release or bridging over) and/or reactivation of the interlock system can thus take place on the basis of data received in a wireless manner in case of a malfunction of the interlock system. For example, the driver is, for example, contacted for this at first over the telephone with a control system, which can effect deactivation or reactivation of the interlock system, depending on how the situation is assessed, for example, by means of data transmitted over a mobile wireless network.

The first analyzing unit and/or the control device advantageously has a memory, which can be written to and read by means of wireless data transmission.

The data being stored in the interlock system can thus be transmitted in a wireless manner to a remote control system, and data can be received from the control system in a wireless manner.

If the quantity of body fluid obtained by the sampling device exceeds the predetermined limit value, this is advantageously indicated by a display on a display unit and/or by an acoustic signal.

The person to be tested, i.e., the driver of the vehicle, can thus recognize when he can end giving the body fluid.

All relevant operations in connection with the use of the interlock system according to the present invention are preferably stored in the memory of the interlock system. The memory can be read by persons or institutions authorized to do so at any desired time. The memory is read, for example, at regular intervals (e.g., once a month) in authorized service shops. The data are then processed by a data management software, and the relevant information is then transmitted (e.g., by email, SMS, mobile telephone or fax) to a monitoring office (e.g., probation officer).

Another advantage of the interlock system according to the present invention is that continued driving of a vehicle can be made possible in case of a technical defect of the interlock system and/or that certain maintenance operations can be performed on the interlock system without having to go to a service shop for this. It is important in this connection that the bridging over of the interlock functionality in case of a defect of the interlock system for continued driving cannot be effected by the driver alone, but at least one person or institution who is authorized to effect a release is involved. The release or deactivation of the interlock system and the subsequent reactivation thereof can take place here by means of a wireless communication between the interlock system and the authorized person or institution, who has access to the control system. The control system may be a data bank accessible by means of a computer or simply a mobile telephone or a fax machine. It can also be achieved by means of the present invention that especially the release functionality in case of a defective interlock system is not part of the (potentially defective) interlock system, but this release functionality is adapted to the interlock system.

The present invention was explained above in general for its application in a motor vehicle. However, it shall be understood that the interlock system according to the present invention can also be used to block the operation of a machine by a user who is under the influence of alcohol, Examples of such machines are large construction equipment, machines in industrial/chemical production plants, power plants, etc.

The present invention will now be described on the basis of some exemplary embodiments with respect to the figures, which show different embodiments of the interlock system according to the present invention. Even though the following description is related to an interlock system that is based on the detection of drugs, the interlock system according to the present invention can also be designed, as is obvious to the person skilled in the art to detect or measure other substances, for example, to detect the alcohol level of the driver.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
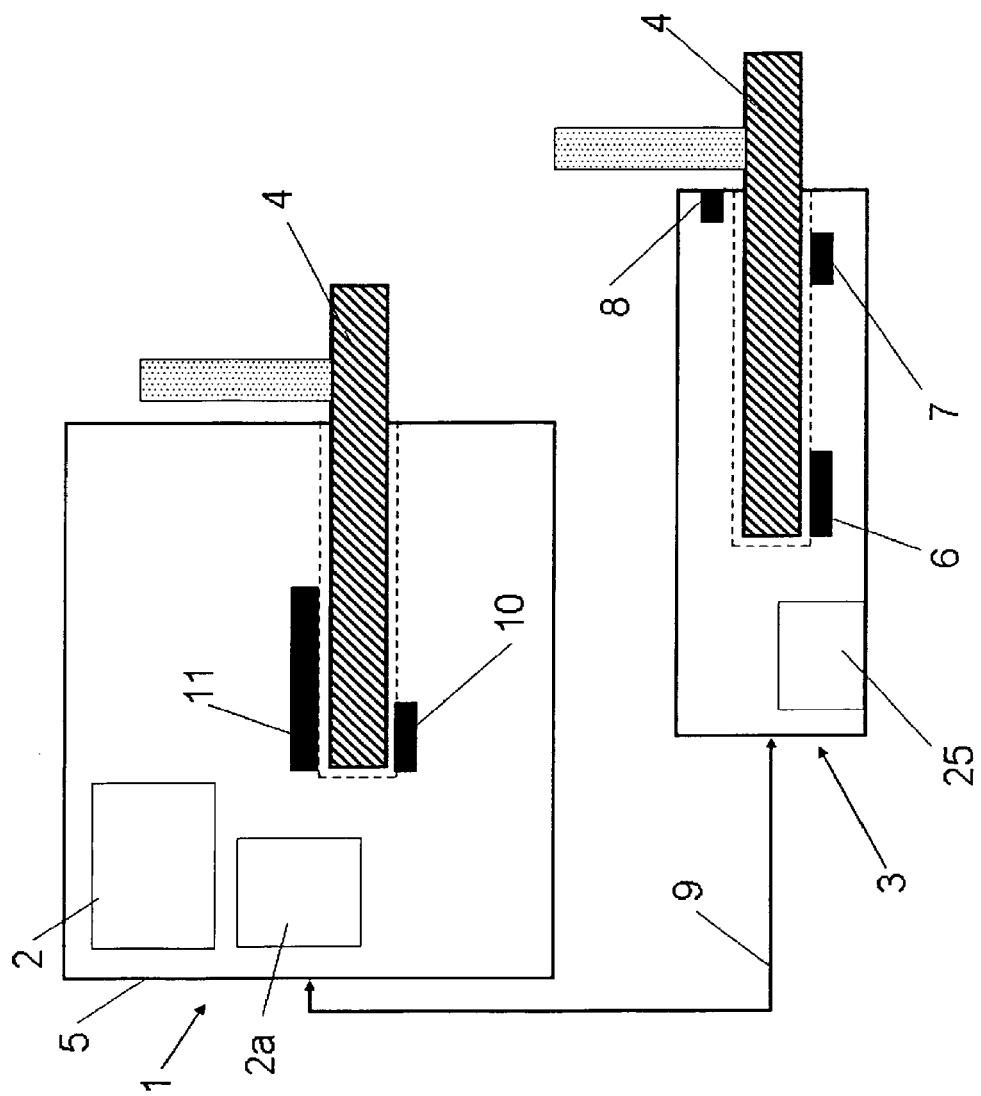
FIG. 1 is a schematic view of the first exemplary embodiment of the drug interlock system according to the present invention, in which first and second analyzing units are located in a housing of the control device and the hand-held device is used for sampling only.

Referring to the drawings in particular, with reference to FIG. 1, a first exemplary embodiment of the present invention will be described below on the basis of an interlock system for a motor vehicle, in which system the analyzing unit is accommodated in the housing of the control device and the hand-held device is only used to receive a sample. The advantage of this embodiment is, among other things, that the hand-held device can be very small and compact.

The drug interlock system according to the present invention contains essentially a control device 1, a first analyzing unit 2, a second analyzing unit 2a, a hand-held device 3 and a sampling device 4. The first analyzing unit 2 and the second analyzing unit 2a are accommodated in the housing 5 of the control device 1. Furthermore, the hand-held device 3 is connected in this embodiment to the control device 1 via an electric cable 9. The first analyzing unit 2 and the second analyzing unit 2a are likewise connected in this embodiment to the respective components of the control device 1 via digital interfaces.

The first analyzing unit 2 and the second analyzing unit 2a may, of course, also be designed as a single analyzing unit, i.e., the functionalities of the first analyzing unit 2 and of the second analyzing unit 2a are provided by a single analyzing unit. The first analyzing unit 2 and/or the second analyzing unit 2a may just as well be accommodated in the hand-held device 3.

As soon as the person (i.e., the male or female driver), who intends to drive the vehicle, actuates the ignition of the vehicle (usually by turning the ignition key into the "ignition" position), the interlock system is put into operation. The system now passes at first through a separate initialization and warm-up procedure. As soon as the interlock system is ready, it reports the state of readiness to the user, for example, by means of an acoustic signal and by a visual display on a display unit 25 of the hand-held device 3, and at the same time it prompts the driver to give a sample.

The display unit may, of course, also be arranged on the housing of the control device 1. Furthermore, the readiness of the interlock system to operate and/or the prompting for giving a sample may also be indicated, as an alternative or in addition to the visual display, with an acoustic signal, for example, by means of a sound or a sequence of sounds.

Before giving the body fluid sample, the driver inserts the sampling device 4 into a corresponding opening of the hand-held device 3. The hand-held device 3 now reads an alphanumeric control sequence or a control sequence in the form of a bar code from the sampling device 4 and transmits this via the cable 9 to the first analyzing unit 2 of the control device 1.

The data transmission between the hand-held device 3 and the control device 1 may, of course, also take place in a wireless manner. The data can be transmitted in this case, for example, by radio, by means of optical signals in the visible or infrared spectral range or even by means of ultrasound.

The control sequence is provided in this embodiment by means of an RFID tag (RFID=Radio Frequency Identification) at the sampling device 4. The alphanumeric control sequence, bar code or RFID tag is preferably located on the underside of the sampling device 4 and is read by means of a corresponding sensor 6, which may be an optical sensor or an RFID sensor, which is provided in the interior of the hand-held device 3 aligned with the opening for the sampling device 4 in a position adjacent to the bar code or RFID tag. As was explained above, different types of sensors can be used, depending on the form in which the control sequence is present at the sampling device 4.

The driver now gives a body fluid sample (for example, saliva sample) into the sampling device 4 inserted into the hand-held device 3. The hand-held device 3 now measures the temperature of the fluid inserted into the sampling device 4 by means of a temperature sensor 7 located in the hand-held device 3. The measured data of the temperature sensor 7 are likewise transmitted to the control device 1 via cable 9. The measured temperature is compared in the control device 1, for example, by the first analyzing unit 2 with a range of desired values. If the measured value is within the range of desired values, it is assumed that the sample was given properly. If the measured value is outside the range of desired values, the body fluid inserted into the sampling device could have been tampered with or not have been given directly by the driver. The control device is designed to prevent the vehicle start process in this case.

After a sufficient quantity of fluid has been applied to or inserted into the sampling device 4, the driver removes the sampling device 4 from the hand-held device 3 and inserts same into a corresponding opening of the control device 1, where an analysis of the chemical components of the saliva is carried out by means of the first analyzing unit 2.

To check whether a sufficient quantity of fluid has been inserted into the sampling device 4, a measuring arrangement, whose mode of operation will be explained later, is provided in the hand-held device 3. The measured data measured automatically by the measuring arrangement 8 during sampling are transmitted to the second analyzing unit 2a via cable 9. If the second analyzing unit 2a determines on the basis of the measured data of the measuring arrangement 8 that a sufficient quantity of body fluid has been given, this is displayed either on the display 25 and/or by an acoustic signal, for example, by a sound or a sequence of sounds.

Blood, urine, tear fluid, sweat or interstitial tissue fluid may, of course, also be used as the body fluid besides saliva.

When the sampling device 4 is inserted into the control device 1, the control sequence or bar code of the sampling device 4 is detected by means of a sensor 10, which corresponds to the sensor 6 of the hand-held device 3 and which is under the control of the first analyzing unit 2, and is transmitted to the first analyzing unit 2 of the control device 1. An algorithm present in the first analyzing unit 2 of the control device 1 compares the control sequences (or RFID data or bar codes) transmitted from the sensor 6 of the hand-held device 3 and those transmitted from the sensor 10 of the control device 1. If these data do not agree, this fact is stored in a memory of control device 1. If the data agree, the analysis of the sample present in the sampling device 4 by the first analyzing unit 2 is initiated by the control device 1. An optical read-out unit 11, whose mode of operation will be explained later, is provided in a suitable position adjacent to the opening in control device 1 for detecting the components of the sample in the sampling device 4.

Figure 2:
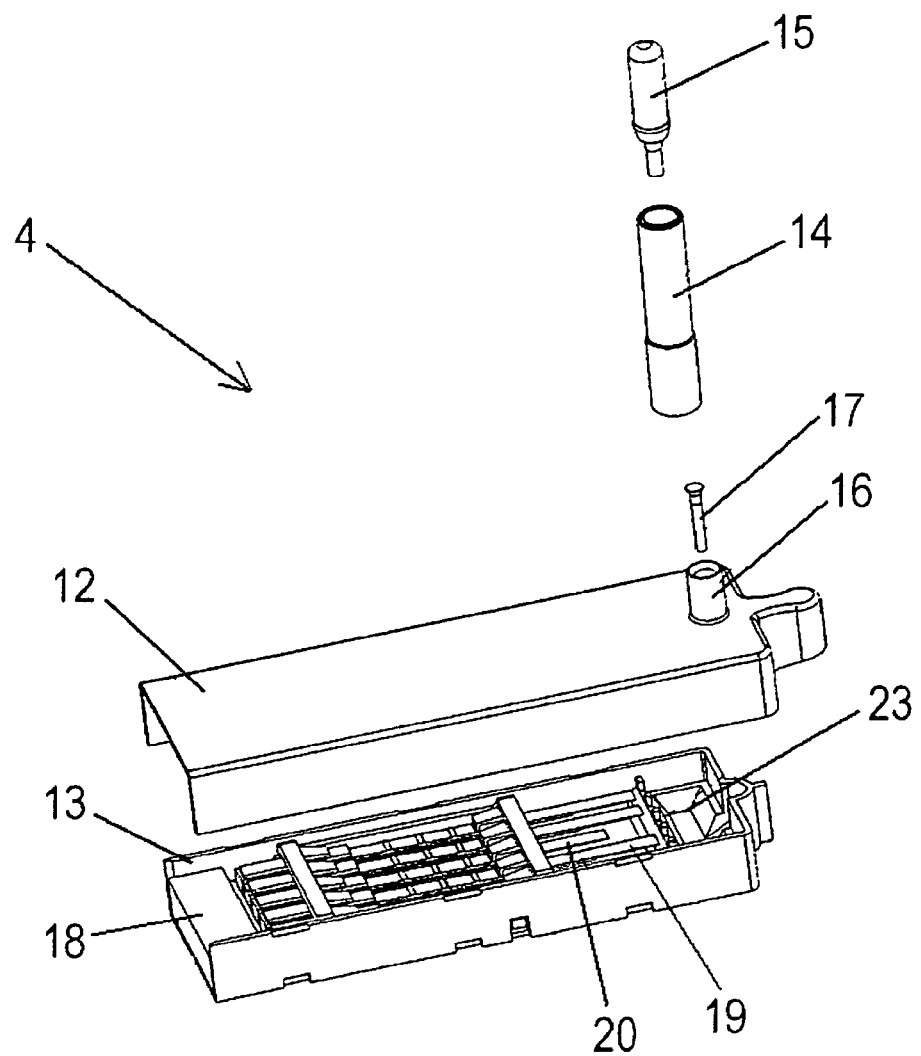
FIG. 2 is a perspective exploded view of a sampling device according to the invention.

FIG. 2 shows an exploded view of a preferred embodiment of the sampling device 4 from FIG. 1. The sampling device has a housing with a top part 12 and with a bottom part 13, an integrated sample receiving device with a mouthpiece holder 14 and with a porous mouthpiece 15, a reagent depot component 17 anchored in the sample opening 16 as well as test strips 19, 20 placed on a carrier plate 18.

The integrated sample receiving device (sampling device) 4 contains a porous mouthpiece 15 for receiving saliva and a mouthpiece holder 14 as a support element for the mouthpiece 15, on the one hand, and as a connection element for transferring the sample into the interior of the housing of the sampling device 4. The saliva sample is taken up in the porous mouthpiece 15 by contact sampling with the oral mucosa and preferably drawn up by capillary forces in the process.

It is necessary, in general, to collect a sufficient volume of saliva. In case of assisted drug tests, this is guaranteed, e.g., by a color change in a specific area of the porous mouthpiece, which can be checked visually by the person to be tested.

Figure 3:
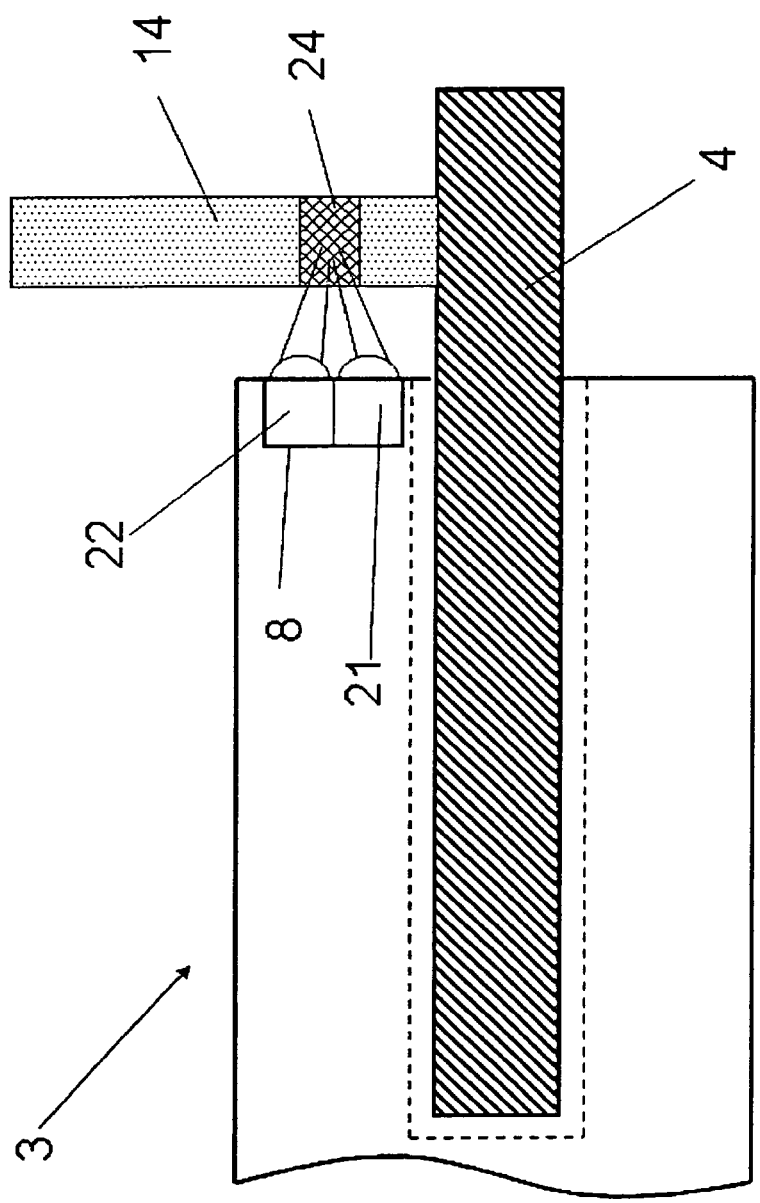
FIG. 3 is a schematic detailed view of an optical detector for the automatic detection of a sufficient quantity of saliva in the sampling device.

FIG. 3 shows an embodiment of a read-out system according to the present invention, which makes it possible to automatically check the volume of saliva during sampling and thus an uninterrupted giving of sample. The read-out method is, for example, an optical read-out method, in which the change in the optical properties of an area of the mouthpiece 15 designed as a detection zone 24 is determined by means of visible light by means of the measuring arrangement 8 shown in FIG. 1. The measuring arrangement 8 arranged in the hand-held device 3 has a light-emitting LED 21 and a photosensitive sensor 22 for this. Whether the optical properties of the detection zone 24 are changed in terms of the intensity of a color change or by means of a change of the reflection properties (change in refractive index without color change) is irrelevant in this exemplary embodiment. If it is a color change, the light emitted by the LED 21 is reflected at the mouthpiece 15 and detected by the photosensitive sensor 22. In case of color change, a change in intensity is measured, whose extent (relative change in intensity) is used to evaluate the volume of the sample. If the change in intensity exceeds a predetermined limit value, a corresponding color change has been brought about by the giving of a sufficient quantity of saliva. The measured data of the measuring arrangement 8, i.e., the measured change in intensity in this exemplary embodiment, are transmitted, as described before, to the second analyzing unit 2a for further processing.

As an alternative, the measuring arrangement 8 may also be designed such that the quantity of sample is checked with other physical or chemical measuring methods, for example, by measuring electrochemical variables or the conductivity of the body fluid.

Especially for measuring electrochemical variables or conductivity, the measuring arrangement 8 may also be arranged in the sampling device 4. In case of arrangement in the sampling device, the measured data can be transmitted from the sampling device 4 to the hand-held device 3, for example, by means of a corresponding contacting. The measured data may also be transmitted from the sampling device 4 to the hand-held device 3 in a wireless manner.

In addition to the volume of the sample, identity features of the sample can be determined in the system in order to increase the safety of the method against tampering. For example, the immunochemical determination of human serum proteins can provided information on both the sample quantities and the origin of the sample. It can be determined based on the chemical composition of the proteins contained in the sample whether the saliva is human saliva. An individualized assignment of the sample to a certain person is possible, for example, on the basis of a molecular genetic profile of the DNA or RNA contained in the body fluid sample. The porous mouthpiece 15 may consist, for example, of foamed materials, pressed or bonded fibers, or sintered plastics, metals or ceramics.

The saliva sample received in the mouthpiece is transferred into the interior space of the housing of the sampling device 4 either passively or actively by means of an actuator (see FIG. 2). This preferably happens by generating an overpressure with a penetrating reagent liquid, which produces, as is described in DE 103 28 984 B4, an extract or filtrate, which contains part of the sample fluid.

A sample tray 23 for holding and tempering the liquid sample is located in the bottom part 13 of the housing of the sampling device 4. The sample tray 23 can be heated or cooled, for example, from the outside by means of the positive-locking connection with a tempering element.

The carrier plate 18 comprises a plurality of mounts for immunochromatographic test strips 19, 20, which are separated from one another in order to prevent the mutual effects ("crosstalk") of the capillary active detection elements on one another. The immunochromatographic test strips 19, 20 consist, in general, of capillary active carrier materials or a composite of different capillary active carrier materials or microfluidic channels, which autonomously make possible a fluid transport after fluid contact has been established with the liquid sample. They are preferably porous layers of polymers or bonded and pressed fibers, which have depot zones or detection zones. The capillary active detection elements consist especially of a test strip material.

The capillary active detection elements are preferably fixed partly on the carrier plate, while another part of the capillary active detection elements protrudes into the test cassette in order to come into fluid contact with the liquid sample.

After fluid contact has become established, the capillary active detection elements become saturated with sample fluid. As a consequence of the fluid flow through the test strip materials, further reagents can be solubilized for the detection reaction of the analytes. Reaction or complexing takes place with the analyte or analytes, which are detected selectively farther upstream in one or more detection zones separated in space by means of immunochemical interaction. The signals in the detection zones can be read, depending on the marker used, optically, magnetically or electrically.

After the analysis of the saliva sample used in this exemplary embodiment, the test result is displayed, in general, with a message such as "Test OK" or Test NOT OK" in case of a negative test result if no target substance was detected or if the concentration of the target substance is below a set concentration limit value. The measured concentration is also displayed in one embodiment. The further vehicle start process is not released in the cases in which the test result is positive, i.e., target substances were detected. This happens by interrupting the feed line from the ignition lock to the starter relay in one embodiment, and by digital interaction of the control device with the electronic bus system of the vehicle in another possible embodiment. A message, which is interpreted by the computer unit of the vehicle as a command not to start the vehicle, is sent in the latter case, e.g., via the CAN or LIN bus (CAN=Control Area Network; LIN=Local Interconnect Network) of the vehicle.

After conclusion of the measuring operation, the sampling device 4 is removed again and stored for the purpose of a later confirmation analysis in a laboratory. Sampling device 4 contains suitable structures, for example, cavities or absorbent materials, which store part of the excess sample fluid as evidence over a period of days to a few months. This makes it possible to perform a later laboratory analysis acceptable in a court of law, which can be retrospectively assigned to the driver of the vehicle based on the identification of the sampling device 4 or of the individual sample (for example, based on DNA profiles).

Figure 4:
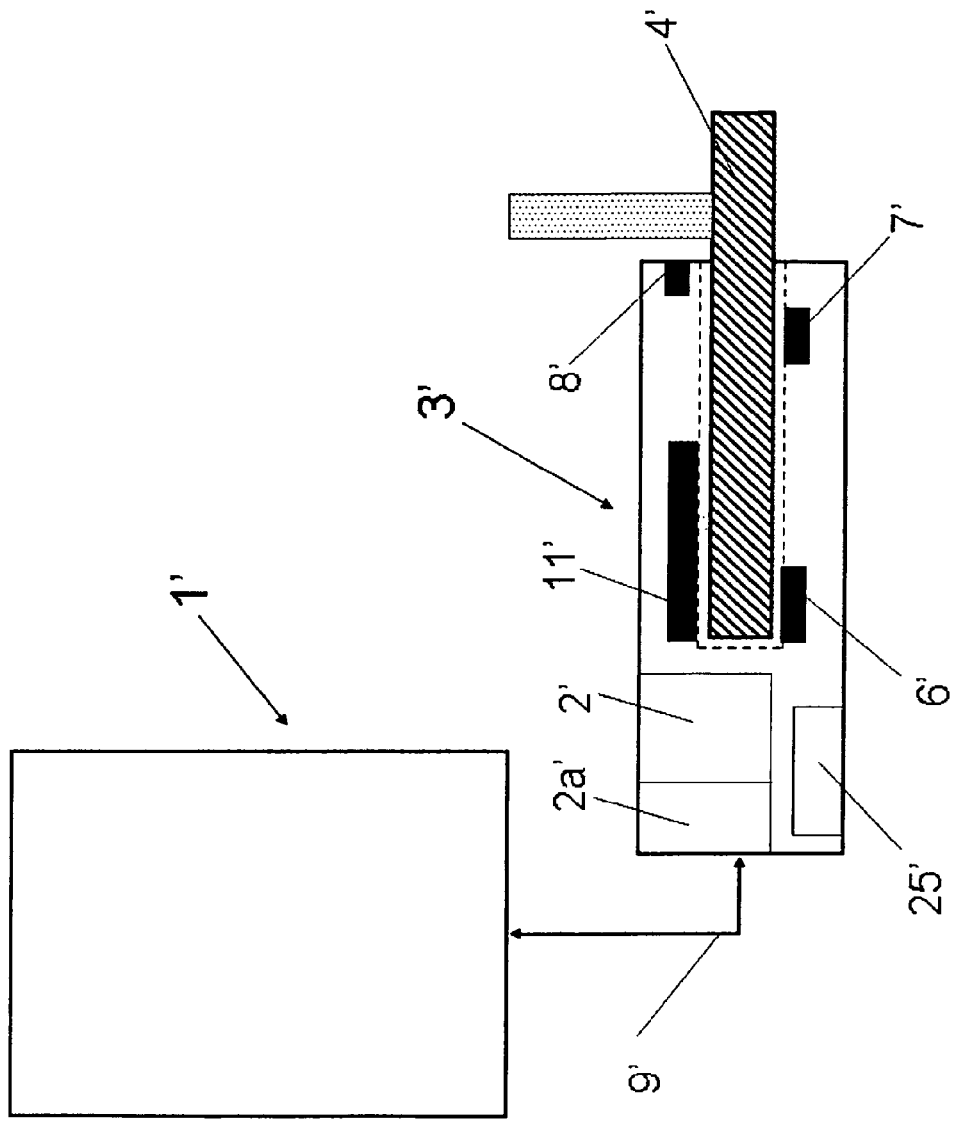
FIG. 4 is a second exemplary embodiment of the drug interlock system according to the present invention, in which first and second analyzing units are located in the hand-held device.

FIG. 4 shows a second embodiment of the present invention, which likewise pertains to an interlock system for motor vehicles, in which the first analyzing unit 2' and the second analyzing unit 2a' are, however, arranged in a housing of the hand-held device 3' and are designed as one structural unit. The analyzing units 2' and 2a' may, of course, also be designed and arranged as separate units. The hand-held device 3' forms a complete substance detector in this embodiment of the present invention, by means of which the sampling and analysis are carried out and which sends the test result obtained with it to the control device F.

The drug interlock system from FIG. 4 has essentially a control device 1', an analyzing device, which can be held in the hand and which is called hand-held device 3', and a sampling device 4'. The hand-held device 3' is connected to the control device 1' by means of a cable 9' in this embodiment as well. The connection between the hand-held device 3' and the control device 1' may, of course, also be a wireless connection as described above in connection with FIG. 1. As soon as the person who intends to drive the vehicle (i.e., the driver) actuates the ignition lock, the interlock system is put into operation. It runs through a separate initialization and warm-up procedure at first.

As soon as the interlock system is ready, it reports the readiness to operate to the driver by a sound signal and/or a display on a display unit 25' of the hand-held device 3' and at the same time prompts the giving of a sample. Before the body fluid sample is given, the driver now inserts the sampling device 4' into the hand-held device 3'. The hand-held device 3' now reads a control sequence from the sampling device 4' and sends same via the cable 9' to the control device F. This control sequence is also arranged, as was described above with reference to FIG. 1, on the sampling device 4', for example, by means of an RFID tag and verifies the particular sampling device by means of a sensor 6' as a valid sampling device. Other information media and corresponding sensors 6' may also be used instead of the RFID tag. The driver now gives a body fluid sample (for example, saliva) into the sampling device. The hand-held device 3' now measures the temperature of the fluid inserted into the sampling device by means of a temperature sensor 7'. The measured temperature is compared in the hand-held device 3' with a range of desired values, for example, by the first analyzing unit 2'. If the measured value is in the range of desired values, the sample is assumed to be a sample having been given properly. If the measured value is outside the range of desired values, the body fluid inserted into the sampling device could have been tampered with or could not have been given directly by the driver. The control device 1' is designed for this case to prevent the vehicle start process.

Measured data, which are an indicator of the quantity of body fluid received by the sampling device, are automatically measured during sampling by means of a measuring arrangement 8', which is designed, for example, as the measuring device 8 according to FIG. 3. It can thus be checked based on the measured data whether the quantity of body fluid taken up by the sampling device 4' exceeds a predetermined limit value. The measured data are transmitted from the measuring arrangement 8' to the second analyzing unit 2a' either via a line, for example, a strip conductor or a cable, or in a wireless manner, for example, by radio, by means of optical signals in the visible or infrared spectral range or even by means of ultrasound, and are analyzed by the second analyzing unit 2a'. If the second analyzing unit 2a' determines that the quantity of body fluid received by the sampling device 4' exceeds a predetermined limit value, the hand-held device 3' begins with the analysis of the sample. The beginning of the analysis of the sample and/or the fact that a sufficient quantity of body fluid has been obtained can be displayed on display unit 25' and/or indicated by an acoustic signal, for example, by a sound or a sequence of sounds.

Sampling device 4' has the same configuration as the sampling device 4, which was explained with reference to FIG. 2 and the corresponding description.

A marked improvement of safety against tampering is achieved, furthermore, by the process of giving a sample being checked by a camera. A camera module is fastened for this in the vehicle such that at least the area of the driver's seat is in the field of view of the camera. It is possible as a result to visually record the person giving the sample (driver of the vehicle) at the time the sample is being given, so that it is recognized whether a mouthpiece of the sampling device 4, 4' is in the driver's mouth during the giving of the sample. It is possible, furthermore, for the point in time at which the sample is given to be unambiguously characterized by feeding a partial flow of the breath sample to an electrochemical sensor by means of, for example, a bellows actuated by a lifting magnet. This suction represents a very short time period of about one second and defines the moment at which the sample is being given with sufficient precision. The collection process is markedly prolonged in case of collecting body fluid, especially saliva, and a time of up to into the minute range can be assumed. It is seen here that it is advantageous to record at least three pictures of the person giving the sample (male or female driver) and to correlate the points in time at which the pictures are taken with the change brought about by the body fluid in the properties of the detection zone, which properties are optical properties in this embodiment. It is seen, furthermore, that it is advantageous to take these pictures at certain points in time, i.e., the first picture at the beginning of the color change of the mouthpiece 15, the second picture in the middle of the color change process, and the third picture at the end or near the end of the color change. This is achieved technically by taking pictures permanently at defined intervals beginning with the giving of the sample, but storing only the pictures that are correlated with the above-described points in time during the color change. It is ensured by the method that a second person cannot give the saliva sample and cannot then pass the nearly full sampling device over to the driver.

Controlling the prompting for body fluid samples combined with a random generator is a measure taken to keep the costs of operating a drug interlock system according to the present invention at a reasonable level for the user and to guarantee at the same time maximum safety for the organization giving the instructions (company, state). The random generator is arranged in the control unit or in a computer system of a monitoring organization, which is or can be connected to the control unit, for example, by means of a radio connection.

Since it is not known to the person (driver) to be tested, who is to be checked, whether he is checked during a certain attempt at starting the vehicle only, he must behave in conformity with the rules during every attempt to start the vehicle and additionally also while driving, because a repeated test may also be coupled to such a random generator besides a first test. This makes carrying a prepared saliva sample of a third person in the mouth of the person to be tested highly inefficient. To increase safety even further, a random generator may also be designed such that the probability of a test is higher in the evenings and at nighttime than in the morning.

Another embodiment is the continuous monitoring in a "home arrest" environment. The analogous technical requirements apply here to the drug-measuring system.

As was explained above, the hand-held device 3, 3' may have a display unit 25, 25' as well as a plurality of control keys. If a driver would like to start his vehicle equipped with an interlock system, he must first switch on the ignition by means of the ignition key. The prompt to give a saliva sample into the mouthpiece 15, 15' of the hand-held device 3, 3' will then appear, for example, on the display unit 25, 25' of the hand-held device 3, 3' (an acoustic signal may additionally sound). The drug concentration is now measured by means of sensor 11, 11' and the first analyzing unit 2, 2' if the second analyzing unit 2a, 2a' determines on the basis of the measured data that the quantity of saliva received by the sampling device exceeds a predetermined limit value and a sufficient quantity of saliva is thus available for an analysis. If the drug concentration is within the defined borderline range, the release is effected, which is displayed by a message on the display unit 25, 25' of the hand-held device 3, 3' (an acoustic signal may additionally sound here as well). The driver can then start the engine by means of the ignition key. During the measurement of the drug concentration, the first analyzing unit 2, 2' generates a signal, which is transmitted to the control device 1, 1'. If the measured drug concentration is within the defined limits, the first analyzing unit 2, 2' generates a corresponding control signal for "switching on" a relay in the ignition circuit between the battery and the starter. If the measured drug concentration is outside these limits, the relay remains switched off, as a result of which the engine is prevented from being started. Alternative control concepts are likewise possible, for example, interfering with the bus system of the motor vehicle, as was explained above. The defined borderline range, within which starting of the engine is permissible, is stored in a memory in the control device 1, 1' itself and can be set permanently and, of course, also changed by an authorized person or by an authorized institution. Furthermore, all relevant data, i.e., the point in time at which an attempt is made at starting the engine, measured drug concentration, possible attempts at tampering, etc., are likewise stored in a memory of the control device 1, 1' or of the first analyzing unit 2, 2' and can be read out by the authorized person or institution. The entering and reading out of data may be carried out by means of a data cable, which is connected to the control device or to the hand-held device, or also in a wireless manner. The control device may contain for this all essential components for a cableless data transmission from/to a remote control system, not shown (for example, computer, server or mobile telephone of an authorized person or institution) and, for example, a safety relay to bridge over the function of the control device 1, 1' of the interlock system in case of a technical disturbance.

The components for cableless data transmission (for example, via UMTS, GSM, GPRS, etc.) are contained in the control device and make it possible to read out a memory in the control device 1, 1' or in the analyzing unit 2, 2' without the need to go to a service shop for this. The communication protocols necessary for the data transmission depend on the type of communication being used (UMTS, GSM, GPRS, etc.) and are known to the person skilled in the art. The data transmission may take place at regular intervals, triggered by a certain event (e.g., a failed drug test, a certain number of drug tests above a certain limit value, an attempt at tampering recorded by the interlock, the expiration of a service or calibration period, etc.) or triggered with a signal (e.g., by SMS or by another suitable protocol) to the interlock system.

The data are handed over here from the memory of the interlock system to a target system (control system, data management system, etc.). The data are stored and possibly processed in this target system. Independently from the transmission of the data from the memory, a notification can be sent by the interlock system directly to the supervisory persons in charge (or to the institution in charge) (e.g., to a mobile telephone or by email/fax) in case of incorrect conduct of the driver (a failed drug test, attempts at tampering, etc.).

The situation that the driver is no longer able to start the engine of his vehicle may occur in case of a defect of the interlock system. This state can be eliminated with a safety relay, which is provided in the control device and is connected in parallel to the functionality proper of the interlock system. It is made possible by such an OR circuit between the safety relay and the function of the interlock system to bypass the blocking interlock system by closing the safety relay. The safety relay is released now by means of wireless data transmission between the communication components of the control device and the remote control system. Two preferred embodiments are conceivable here. In a first embodiment, the control device has a transmitter/receiver (transceiver) in the form of a mobile telephone submodule. The control device is thus able, for example, to receive an SMS (Short Message Service) and to check the sender of this SMS as well as the content of the SMS. The driver of the vehicle must report to a person/authority authorized to effect release in this embodiment. This authority now sends an SMS with a release code to the mobile telephone submodule of the interlock module, for example, via an aforementioned mobile telephone. The software, which is stored and can be executed in the module, then checks, for example, whether the release code and the sending mobile telephone are authorized. Methods that are known to the person skilled in the art and will not be explained in more detail here are used for this. If authorization of the release code is recognized and confirmed, the module subsequently bridges over the interruption of the starter circuit by means of the safety relay by the safety relay being closed.

The release code is transmitted by means of GPRS (General Packet Radio Service) in another preferred embodiment. The quantity of information transmitted in one packet is potentially larger with the use of GPRS, and it is therefore possible to transmit not only a release code having practically any desired length but, moreover, additional information. This information includes, among other things, the time limit of the period over which bridging over is possible.

It is, furthermore, made possible by the wireless data transmission to perform "remote maintenance," i.e., self tests of the interlock system or the resetting of timers or locks (e.g., if the interlock was set to a "lockout mode" after violations, which no longer permits a restarting of the vehicle). In addition, service data in the interlock memory as well as parameter settings (e.g., limit values, etc.) can be read and overwritten and the software of the device can be updated.

While specific embodiments of the invention have been shown and described in detail to illustrate the application of the principles of the invention, it will be understood that the invention may be embodied otherwise without departing from such principles.

The invention claimed is:

1. An interlock system for a vehicle, the interlock system comprising:
   a sampling device, which receives a sufficient body fluid sample from a person to be tested;
   a read-out unit coupled to the sampling device for detecting substances that are contained in the body fluid sample;
   a first analyzing unit coupled to the read-out unit for analyzing the substances detected by the read-out unit to obtain respective concentrations of the detected substances, wherein the detection and analysis of the substances in the body fluid is carried out by means of chemical, immunochemical, enzymatic, electrochemical or optical detection method;
   a second analyzing unit;
   a measuring arrangement for an automatic measurement of measured data, which are an indicator of a quantity of body fluid received by the sampling device, wherein the measuring arrangement transmits the measured data to the second analyzing unit, and wherein the second analyzing unit determines, on the basis of the measured data, whether the quantity of body fluid received by the sampling device exceeds a predetermined limit value; and
   a control device coupled to the first analyzing unit and the second analyzing unit and which prevents a vehicle start process if the quantity of body fluid received does not exceed the limit value or if at least one of the substance concentrations is above or below a predetermined concentration limit value.

2. An interlock system in accordance with claim 1, in which the body fluid is blood, urine, saliva, tear fluid sweat or interstitial tissue fluid.

3. An interlock system in accordance with claim 1, in which a temperature of the body fluid given is measured during the giving of the sample and is compared with a range of desired values.

4. An interlock system in accordance with claim 1, in which the measured data are an indicator of a color change or a change in a refractive index of a detection zone of the sampling device, of electrochemical properties of the body fluid or of a conductivity of the body fluid.

5. An interlock system in accordance with claim 1, in which the substances belong to a group that comprises illegal drugs, including at least one of amphetamines, methamphetamines, opiates, cocaine and cannabinoids, or to a group that comprises therapeutic drugs, including at least one of benzodiazepines, methadone, buprenorphine, and tricyclic antidepressants.

6. An interlock system in accordance with claim 1, in which the sampling is monitored by means of a camera by optically determining whether a mouthpiece of the sampling device is in the mouth of a driver during sampling.

7. An interlock system in accordance with claim 1, in which sampling is monitored by determining, by a biochemical detection reaction whether the sample is human saliva or the saliva of an individual driver.

8. An interlock system in accordance with claim 1, in which points of time at which a measurement is performed are determined by means of a random generator.

9. An interlock system in accordance with claim 1, in which the sampling device is designed to be inserted into the control device or into a hand-held device connected to the control device.

10. An interlock system in accordance with claim 1, in which the control device has a first relay, which is coupled to a starter of the vehicle and which is switched depending on the measured substance concentration, and in which the control device has a second relay, which is connected in parallel to the first relay and can be switched in response to data received in a wireless manner.

11. An interlock system in accordance with claim 1, in which the first analyzing unit and/or the control device has a memory, which can be written to and read out by means of wireless data transmission.

12. An interlock system in accordance with claim 1, further comprising a display on a display unit and/or an acoustic signal generator for indicating if the quantity of body fluid received by the sampling device exceeds the predetermined limit value.

13. An interlock system for a vehicle, the interlock system comprising:
   a sampling device receiving a body fluid sample from a person to be tested;
   a read-out unit operatively connected to the sampling device, the read-out unit detecting substances that are contained in the body fluid sample;
   a first analyzing unit operatively connected to the read-out unit, the first analyzing unit analyzing the substances detected by the read-out unit, and obtaining respective concentrations of the substances detected, wherein the detection and analysis of the substances in the body fluid is carried out by means of chemical, immunochemical, enzymatic, electrochemical or optical detection methods;
   a measuring arrangement for an automatic measurement of a quantity of the body fluid sample obtained by the sampling device to provide measured data;
   a second analyzing unit determining, on the basis of the measured data, whether the quantity of body fluid obtained by the sampling device exceeds a predetermined limit value, the measuring arrangement transmitting the measured data to the second analyzing unit; and
   a control device operatively connected to the first analyzing unit and operatively connected to the second analyzing unit, the control device preventing a vehicle start process if the quantity of body fluid obtained does not exceed the limit value or if at least one of the substance concentrations is above or below a predetermined concentration limit value.

14. An interlock system in accordance with claim 13, wherein the body fluid of the body fluid sample is blood, urine, saliva, tear fluid sweat or interstitial tissue fluid.

15. An interlock system in accordance with claim 13, wherein the measuring arrangement measures a temperature of the body fluid of the body fluid sample, during the giving of the sample, and the temperature is compared with a range of desired values.

16. An interlock system in accordance with claim 13, wherein sampling is monitored by determining, by a biochemical detection reaction, whether the sample is human saliva or the saliva of an individual driver.

17. An interlock system in accordance with claim 13, wherein:
the control device has a first relay, which is coupled to a starter of the vehicle, the first relay being switched depending on the measured substance concentration; and
the control device has a second relay, which is connected in parallel to the first relay and can be switched in response to data received in a wireless manner.

18. An interlock system in accordance with claim 17, wherein at least one of the first analyzing unit and the control device has a memory, which can be written to and read out by means of wireless data transmission.

19. An interlock system in accordance with claim 13, further comprising a display unit with a display, the display indicating a quantity of body fluid received by the sampling device exceeds the predetermined limit value.

20. An interlock system operation method for a vehicle, the method comprising:
providing an interlock system with a sampling device receiving a body fluid sample from a person to be tested, a read-out unit operatively connected to the sampling device, the read-out unit detecting substances that are contained in the body fluid sample, a first analyzing unit operatively connected to the read-out unit, the first analyzing unit analyzing the substances detected by the read-out unit, and obtaining the respective concentrations of the substances detected, wherein the detection and analysis of the substances in the body fluid is carried out by means of chemical, immunochemical, enzymatic, electrochemical or optical detection methods, a measuring arrangement for an automatic measurement of a quantity of the body fluid sample obtained by the sampling device to provide measured data, a second analyzing unit determining, on the basis of the measured data whether the quantity of body fluid obtained by the sampling device exceeds a predetermined limit value, the measuring arrangement transmitting the measured data to the second analyzing unit and a control device operatively connected to the first analyzing unit and operatively connected to the second analyzing unit, the control device preventing a vehicle start process if the quantity of body fluid obtained does not exceed the limit value or if at least one of the substance concentrations is above or below a predetermined concentration limit value;
switching on an ignition of the vehicle;
with the interlock system prompting a driver of the vehicle to provide a body fluid sample;
determining, with the interlock system, the quantity of the body fluid obtained and the concentration of the substances detected, independently from one another;
with the control unit, determining whether a starter of the vehicle will be released and an engine can be started, or preventing the engine from being started if at least one of the following situations is present:
the quantity of body fluid obtained does not exceed the predetermined limit value; and
at least one of the substance concentrations is above or below a predetermined concentration limit value.

* * * * *